(12) United States Patent  (10) Patent No.: US 8,757,802 B2
Kamada  (45) Date of Patent: Jun. 24, 2014

(54) LIGHT INTENSITY CONTROL APPARATUS, LIGHT INTENSITY CONTROL METHOD, PROGRAM, AND OPHTHALMOLOGIC APPARATUS

(75) Inventor: Shohhei Kamada, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 195 days.

(21) Appl. No.: 13/217,509

(22) Filed: Aug. 25, 2011

(65) Prior Publication Data

US 2012/0050680 A1    Mar. 1, 2012

(30) Foreign Application Priority Data

Aug. 31, 2010  (JP) .................................. 2010-194512

(51) Int. Cl.
*A61B 3/14* (2006.01)
*A61B 3/10* (2006.01)
*A61B 3/00* (2006.01)
*A61B 3/12* (2006.01)

(52) U.S. Cl.
CPC .................. *A61B 3/14* (2013.01); *A61B 3/0008* (2013.01); *A61B 3/12* (2013.01)
USPC .......................................... 351/206; 351/221

(58) Field of Classification Search
USPC .......................................... 351/205–210, 221
See application file for complete search history.

(56) References Cited

U.S. PATENT DOCUMENTS

| | | | |
|---|---|---|---|
| 4,690,525 A | 9/1987 | Kobayashi et al. | |
| 5,530,494 A | 6/1996 | Ogawa et al. | |
| 6,244,710 B1 | 6/2001 | Ogawa | |
| 2012/0050515 A1* | 3/2012 | Shikaumi et al. | 348/78 |

FOREIGN PATENT DOCUMENTS

| | | | |
|---|---|---|---|
| JP | 60-137347 A | | 7/1985 |
| JP | 61-203937 A | | 9/1986 |
| JP | 02-237536 A | | 9/1990 |
| JP | 03-114434 A | | 5/1991 |
| JP | 04-150831 A | | 5/1992 |
| JP | 05-192299 A | | 8/1993 |
| JP | 08-033612 A | | 2/1996 |
| JP | 11-238129 A | | 8/1999 |
| JP | 2000-107133 A | | 4/2000 |
| JP | 2000-197608 A | | 7/2000 |
| JP | 2001-258852 A | | 9/2001 |
| JP | 2003-010134 A | | 1/2003 |
| JP | 2005-261447 A | | 9/2005 |
| JP | 2005-261449 A | | 9/2005 |
| JP | 2005261449 A | * | 9/2005 |
| JP | 2005-270152 A | | 10/2005 |
| JP | 2005-279154 A | | 10/2005 |

* cited by examiner

*Primary Examiner* — Mahidere Sahle
(74) *Attorney, Agent, or Firm* — Fitzpatrick, Cella, Harper & Scinto

(57) ABSTRACT

Provided is a light intensity control apparatus including: a photometry value calculation portion for measuring reflected light from a fundus under illumination of an observation light source; an observation light source control portion for controlling a light intensity of the observation light source based on photometry information obtained by the photometry value calculation portion, the light intensity of the observation light source obtained in the measurement, and a correction value of the light intensity of the observation light source; and a photographing light source control portion for controlling a light intensity of a light source of a photographing light source based on the photometry information obtained by the photometry value calculation portion, the light intensity of the observation light source obtained in the measurement, and a correction value of the light intensity of the photographing light source.

17 Claims, 6 Drawing Sheets

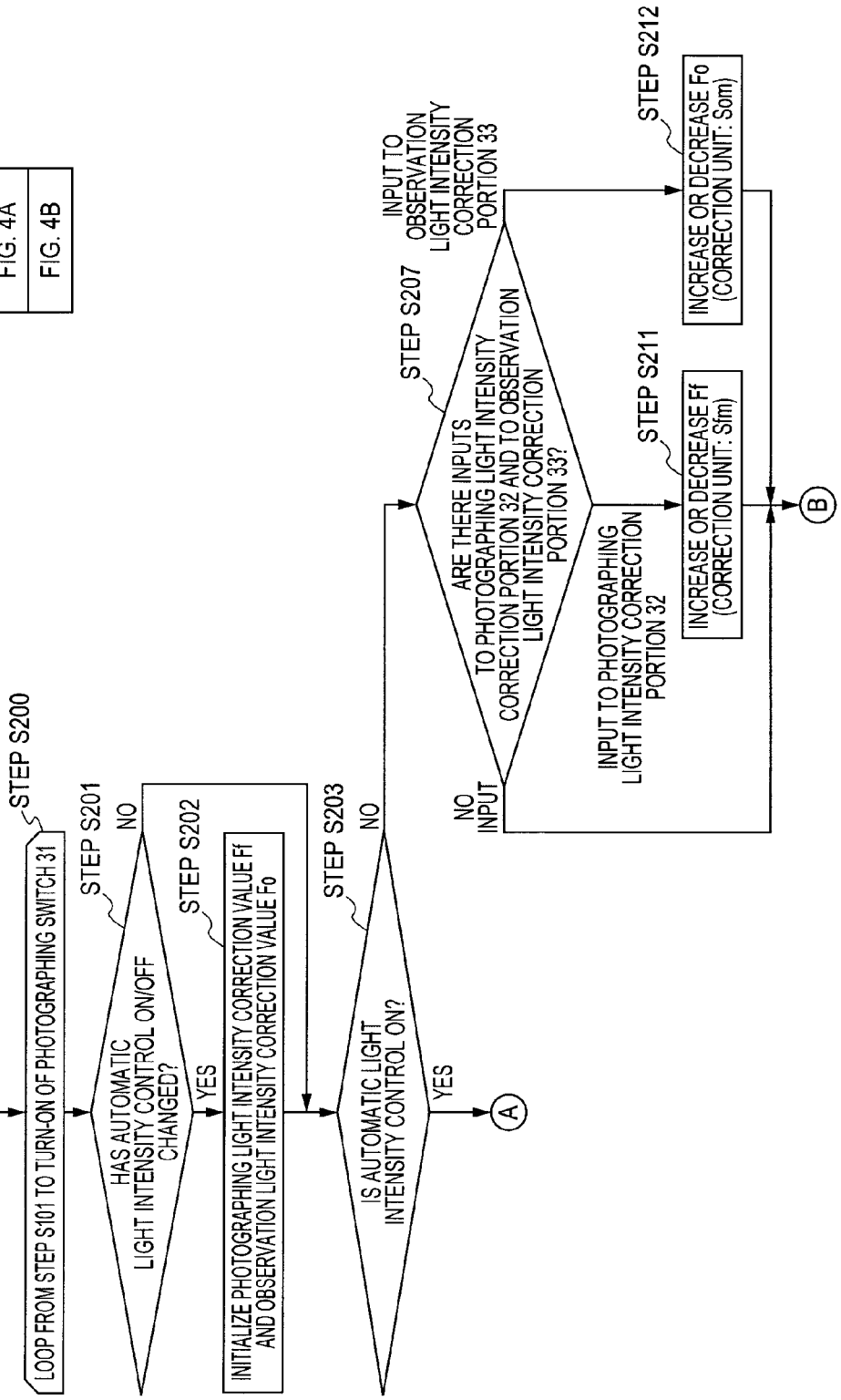

LIGHT INTENSITY CONTROL APPARATUS, LIGHT INTENSITY CONTROL METHOD, PROGRAM, AND OPHTHALMOLOGIC APPARATUS

BACKGROUND OF THE INVENTION

1. Field of the Invention

The present invention relates to a technology for controlling light intensity of a light source when a fundus image is observed or taken.

2. Description of the Related Art

Conventionally, there has been known an ophthalmologic photographing apparatus configured as follows. A fundus of an eye to be inspected is irradiated by observation light that is steady light. A fundus image under the observation light, which is obtained by receiving reflected light from the fundus, is aligned while being observed. After that, photographing light, which is pulsed light, is projected so as to obtain a fundus image under the photographing light as a still image. The light reflectance of the fundus is different among individual eyes to be inspected, due to individual variation, lesion or the like. Therefore, it is necessary to provide a technology for appropriately controlling light intensity of the photographing light to be received by the photographing element.

As an example of such a technology, Japanese Patent Application Laid-Open No. H04-150831 discloses a technology of irradiating an eye to be inspected with the observation light and determining the light intensity of the photographing light based on the observation light reflected by the fundus.

However, in the technology disclosed in Japanese Patent Application Laid-Open No. H04-150831, light intensity control is performed only for a photographing light source. In the ophthalmologic photographing apparatus, it is also necessary to control the light intensity of the observation light when the fundus is observed under the observation light. However, in the technology disclosed in Japanese Patent Application Laid-Open No. H04-150831, it is necessary for an operator to appropriately adjust the light intensity of the observation light source manually while observing and aligning the fundus image in fundus observation.

In addition, the technology disclosed in Japanese Patent Application Laid-Open No. H04-150831 is aimed at taking a fundus image with appropriate light intensity. However, the appropriate light intensity in the fundus photographing varies due to various factors including the purpose of photographing, taste of a reader of the fundus image. The technology disclosed in Japanese Patent Application Laid-Open No. H04-150831 cannot perform the light intensity control flexibly to meet such a necessity. The same is true for observation light intensity. As to brightness of the fundus image to be observed, for example, if the fundus image is darker, it is usually easier to view an alignment index projected to the eye to be inspected for alignment, resulting in easier operation. Therefore, it is necessary to decrease the observation light intensity. However, on the contrary, when the fundus image is observed under the observation light, it is considered that the observation of the fundus image is easier under higher intensity of light. Therefore, it is necessary for the appropriate value of fundus image exposure to be set flexibly even in the case where automatic control of observation light intensity is performed.

SUMMARY OF THE INVENTION

In view of the above, an object of the present invention is to control light intensity of a light source so as to achieve an appropriate exposure value according to specific purpose and use when a fundus image is observed and taken.

According to the present invention, a light intensity control apparatus includes: a photometry unit for measuring reflected light from a fundus under illumination of a first light source for observing the fundus; a first control unit for controlling a light intensity of the first light source based on photometry information obtained by the photometry unit, the light intensity of the first light source obtained in the measurement by the photometry unit, and a correction value of the light intensity of the first light source; and a second control unit for controlling a light intensity of a second light source based on the photometry information obtained by the photometry unit, the light intensity of the first light source in the measurement by the photometry unit, and a correction value of the light intensity of the second light source for photographing the fundus. According to the present invention, an ophthalmologic apparatus includes: an observation light source for observing an eye to be inspected; a photographing light source for photographing the eye to be inspected; a photometry unit for measuring return light from the eye to be inspected, which is irradiated by observation light from the observation light source; and a control unit for controlling a light intensity of the observation light source and a light intensity of the photographing light source independently based on photometry information obtained by the photometry unit.

According to the present invention, it is possible to control the light intensity of the light source so as to achieve an appropriate exposure value according to specific purpose and use when the fundus image is observed and taken.

Further features of the present invention will become apparent from the following description of exemplary embodiments with reference to the attached drawings.

DESCRIPTION OF THE EMBODIMENTS

Hereinafter, a preferred embodiment of the present invention is described in detail with reference to the attached drawings.

Figure 1:
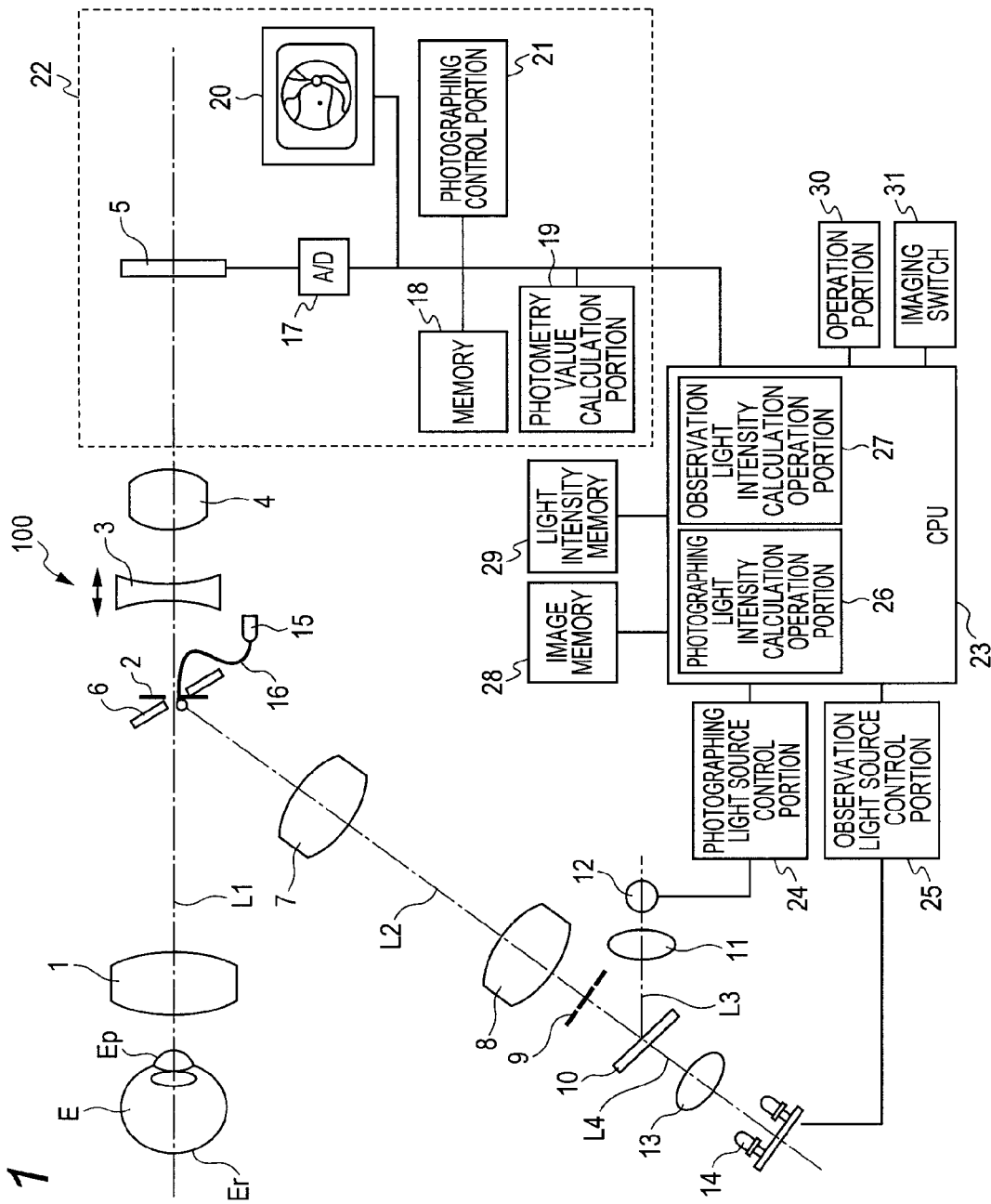
FIG. 1 is a diagram illustrating a structure of a fundus camera according to an embodiment of the present invention.

First, the embodiment of the present invention is described. FIG. 1 is a diagram illustrating a structure of a fundus camera 100 according to the embodiment of the present invention. In FIG. 1, an observation photographing optical system includes an objective lens 1 disposed to be opposed to an eye E to be inspected, a photographing aperture stop 2 disposed on an optical axis L1 of the objective lens 1, a focus lens 3, and an image-forming lens 4, and guides reflected light from the fundus to a photographing element 5. When the observation light is projected, the observation photographing optical system guides the reflected light of the observation light from the fundus to the photographing element 5. When the photographing light is projected, the observation photographing optical system guides the reflected light of the photographing light from the fundus to the photographing element 5. Note that the fundus camera 100 has a structure to be an application example of a light intensity control apparatus.

A photographing portion 22 includes the photographing element 5 having sensitivity to the photographing light and the observation light, an A/D converter element 17, a memory 18, a photometry value calculation portion 19, a monitor 20, and a photographing control portion 21. The photographing portion 22 is fixed to a casing of an optical portion of the fundus camera at a mount portion (not shown) in a detachable and attachable manner. By using the observation photographing optical system and the photographing portion 22, the fundus is irradiated to thereby take a fundus image.

A fundus illumination optical system includes the objective lens 1, an aperture mirror 6, a lens 7, a lens 8, a ring aperture stop 9, a dichroic mirror 10, a condenser lens 11, and a condenser lens 13. The fundus illumination optical system guides the observation light and the photographing light to the eye E to be inspected. The aperture mirror 6 is disposed obliquely in the vicinity of the photographing aperture stop 2. On an optical axis L2 in the reflection direction of the aperture mirror 6, there are disposed the lens 7 and the lens 8. In addition, on the aperture mirror 6, a WD light source 15 for projecting an alignment index to a cornea Ep of the eye E to be inspected is connected via a fiber 16. The WD light source 15 is a light source having a very narrow wavelength band or substantially a single wavelength of 700 nm. Note that a light source having another wavelength band may be used.

The ring aperture stop 9 having a ring-like aperture has a light blocking portion around the optical axis and is disposed substantially at an optically conjugate position of the pupil Ep of the eye E to be inspected via the lens 7 and the lens 8. The dichroic mirror 10 has a characteristic of transmitting the wavelength band of the observation light while reflecting the wavelength band of the photographing light, and is disposed on the optical axis L2 together with the ring aperture stop 9. On an optical axis L3 of the dichroic mirror 10 in the reflection direction, there are disposed the condenser lens 11 and a photographing light source 12. On an optical axis L4 of the dichroic mirror 10 in the transmission direction, there are disposed the condenser lens 13 and an observation light source 14.

The photographing light source 12 is a light source for projecting photographing pulsed light to the eye E to be inspected. The photographing light source 12 is controlled by a photographing light source control portion 24. The observation light source 14 includes a plurality of arranged LEDs, projects steady light to the eye E to be inspected, and is controlled by an observation light source control portion 25. Here, the photographing light source means a light source irradiating the fundus for taking a target fundus image, and the observation light source means a light source irradiating the eye E to be inspected for photographing preparation such as alignment between the fundus camera 100 and the eye E to be inspected before taking the target fundus image. Using a moving image of the fundus image obtained by projecting the observation light before projecting the photographing light for the real photographing, an inspector observes the fundus and adjusts the positional alignment, the focusing, and other photographing conditions. In this embodiment, the photographing light source 12 is a light source having a wide-band wavelength of 420 to 750 nm, and the observation light source 14 is a light source having a very narrow wavelength band or substantially a single wavelength of 850 nm. Adopting an infrared wavelength light source as the observation light source 14, miosis at the time of observation can be suppressed. By using the fundus illumination optical system, the photographing light source 12, and the observation light source 14, the eye E to be inspected is irradiated with the observation light and the photographing light, and the fundus is illuminated. Note that the observation light source 14 is an application example of a first light source, and the photographing light source 12 is an application example of a second light source. In addition, the observation light source control portion 25 is an application example of a first control unit, and the photographing light source control portion 24 is an application example of a second control unit.

The above-mentioned structure is housed in one casing so as to constitute the optical portion of the fundus camera. Further, the optical portion of the fundus camera is mounted on a sliding table (not shown), which enables alignment with the eye E to be inspected.

A central control unit 23 is constituted of a CPU or the like and controls the entire fundus camera 100. The central control unit 23 functions as a photographing light intensity calculation operation portion 26 and an observation light intensity calculation operation portion 27. The central control unit 23 is connected to the photometry value calculation portion 19, an image memory 28, a light intensity memory 29, an operation portion 30, a photographing switch 31, and the like.

The photographing light intensity calculation operation portion 26 and the observation light intensity calculation operation portion 27 respectively determine light intensities of the photographing light source 12 and the observation light source 14 based on a photographing light intensity correction value Ff and an observation light intensity correction value Fo input by the operator with a photographing light intensity correction portion 32 and an observation light intensity correction portion 33 described later, respectively, a photometry value S as photometry information output from the photometry value calculation portion 19, and intensity information of the observation light emitted from the observation light source 14 to irradiate the eye E to be inspected. Here, the light intensity means radiation energy irradiating a unit area for a certain period of time, which is a time integral of a light beam Φ over a certain given period of time Δt. In the fundus camera 100 according to this embodiment, a shutter (not shown) is opened in a period from before light emission until after light emission of the observation light source 14 and the photographing light source 12, and the observation light source 14 adjusts its light intensity so that light intensity of the photographing light to be received by the sensor is adjusted. In addition, the photographing light source 12 adjusts a period of time of emitting the photographing light so that light intensity of the photographing light to be received by the sensor is adjusted.

Figure 2:
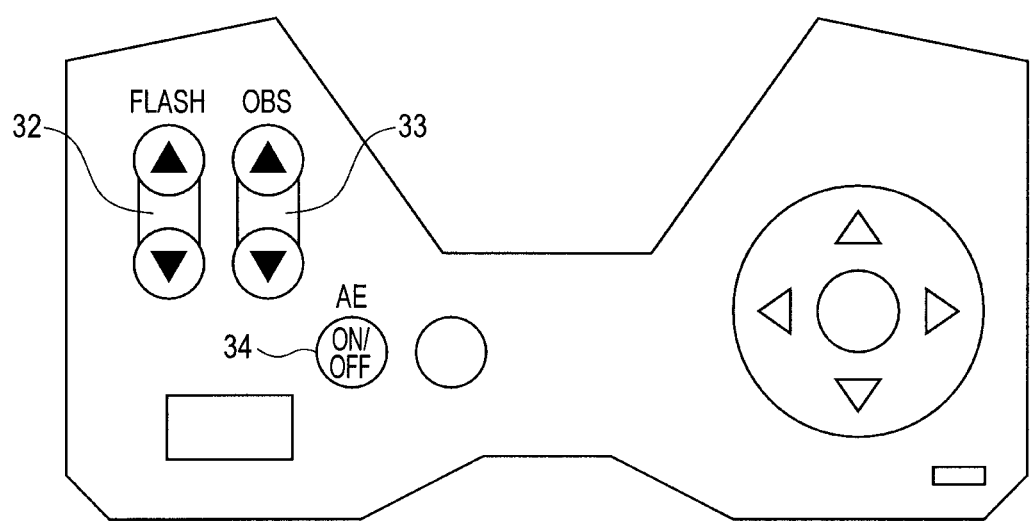
FIG. 2 is a diagram illustrating an example of an operation portion.

The operation portion 30 is provided for the inspector to input an instruction. The operation portion includes at least the photographing light intensity correction portion 32, the observation light intensity correction portion 33, and a light intensity control switching portion 34. The operation portion 30 is constituted of a joystick, a dial, a switch, or the like, for example. FIG. 2 is a diagram illustrating an example of the operation portion 30. In the example of FIG. 2, the photographing light intensity correction portion 32, the observation light intensity correction portion 33, and the light intensity control switching portion 34 are switches that can be pressed by the operator. The photographing light intensity correction portion 32 is used for light intensity correction in automatic photographing light intensity control or light intensity setting in manual light intensity control, and hence is constituted of two independent switches so that the light intensity can be increased or decreased as the correction. The observation light intensity correction portion 33 also has the same structure. In addition, as to other operation portions, the joystick (not shown) is operated toward front, rear, left, or right viewed from the inspector so that a positional relationship between the eye E to be inspected and the main body of the fundus camera 100 can be adjusted in the front, rear, left and right directions. Further, the dial is turned so that the positional relationship between the eye E to be inspected and the main body of the fundus camera can be adjusted in the vertical direction. Note that the observation light intensity correction portion 33 is an application example of the first input unit, the photographing light intensity correction portion 32 is an application example of the second input unit, and the light intensity control switching portion 34 is an application example of the switching unit.

Figure 3:
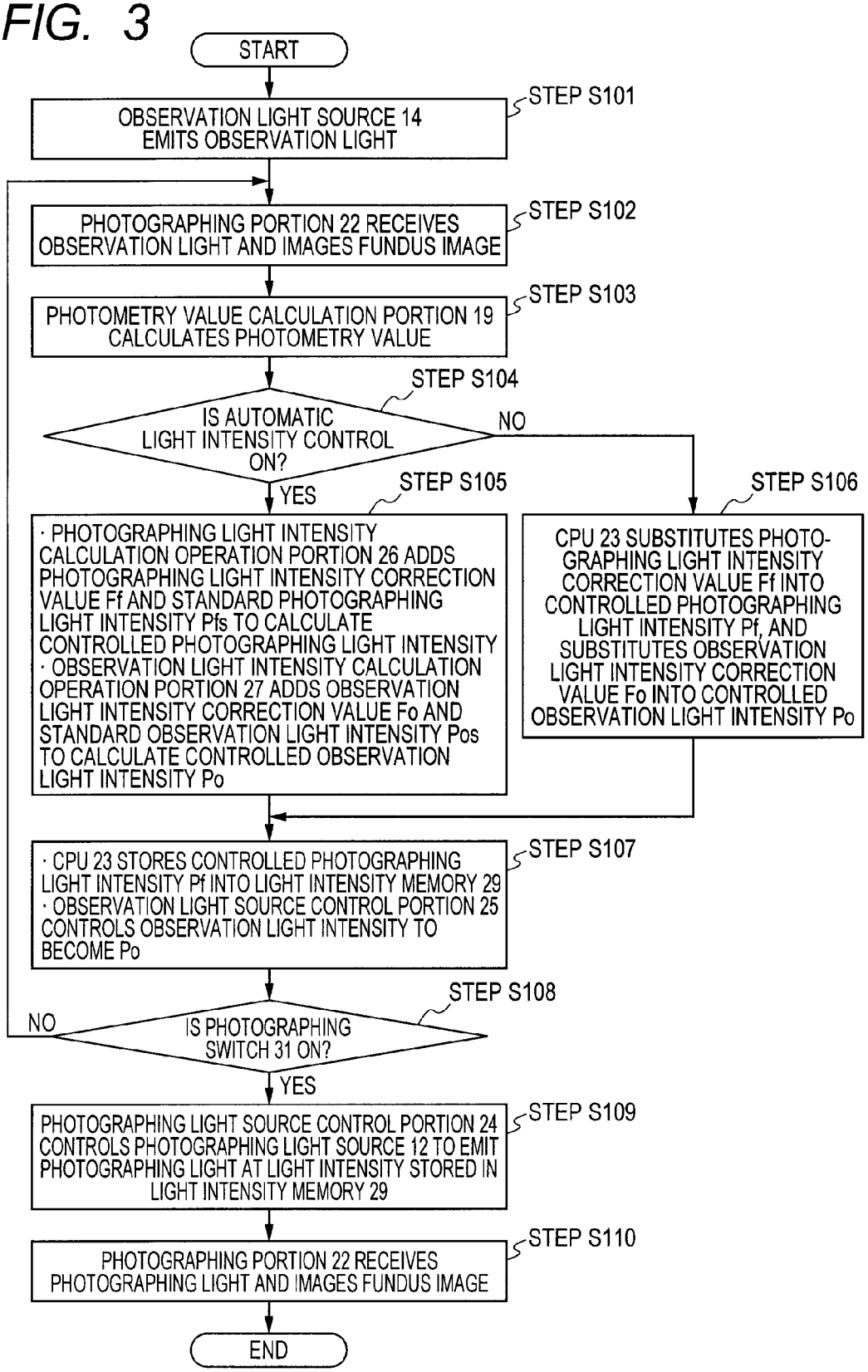
FIG. 3 is a flowchart of a process of the fundus camera according to the embodiment of the present invention.

Next, a process of the fundus camera 100 according to this embodiment is described. FIG. 3 is a flowchart illustrating the process of the fundus camera 100 according to this embodiment.

In Step S101, the observation light source 14 emits the observation light. The observation light emitted by the observation light source 14 irradiates a fundus Er of the eye E to be inspected. The steady light emitted from the observation light source 14 irradiates the fundus Er, and the reflected and scattered light beam from the fundus Er goes out from the eye E to be inspected through the pupil Ep and reaches the photographing element 5. The photographing portion 22 including the photographing element 5 receives the light that has reached the photographing element 5 so as to take a fundus image (Step S102). In this process, each pixel of the photographing element 5 receives the observation light and outputs an electric signal corresponding to each received light intensity. The output from each pixel is A/D converted by the A/D converter element 17 and is stored as fundus image data in the memory 18. In addition, the output from the photographing element 5 as a digital signal is output to the monitor 20 via the photographing control portion 21. Note that the fundus image data stored in the memory 18 may be displayed on the monitor 20. Thus, the fundus image is displayed on the monitor 20. The received light intensity of the observation light source 14 is adjusted by the automatic control by the fundus camera 100 or the operator operating the operation portion 30 so that the fundus image displayed on the monitor 20 has an appropriate brightness. In addition, the WD light source 15 projects the alignment index to the cornea Ep of the eye E to be inspected via the fiber 16. The operator uses the joystick (not shown) and refers to the projected alignment index so as to perform alignment between the eye E to be inspected and the optical portion of the fundus camera. Further, a position of the focus lens 3 in the optical axis direction is adjusted by operating a focus knob (not shown), and a focus of the displayed fundus image is adjusted.

In Step S103, the photometry value calculation portion 19 calculates an average pixel value of the entire fundus as a photometry value S from the fundus image data stored in the memory 18. The calculated photometry value S is output to the photographing light intensity calculation operation portion 26 and the observation light intensity calculation operation portion 27.

Next, a method of determining the observation light intensity and the photographing light intensity is described. Controlled photographing light intensity Pf, which is light intensity for performing actual photographing, is calculated by adding a standard photographing light intensity Pfs determined automatically from a fundus reflection characteristic of the eye E to be inspected and a photographing light intensity correction value Ff. In addition, a controlled observation light intensity Po, which is light intensity for performing actual observation, is calculated by adding a standard observation light intensity Pos determined automatically from the fundus reflection characteristic of the eye E to be inspected and an observation light intensity correction value Fo.

The photographing light intensity correction value Ff and the observation light intensity correction value Fo, which are elements for determining the photographing light intensity and the observation light intensity, respectively, are changed in value according to inputs of the photographing light intensity correction portion 32 and the observation light intensity correction portion 33 that can be operated by the operator. In addition, the values can also be changed by operation of the light intensity control switching portion 34.

Figure 4B:
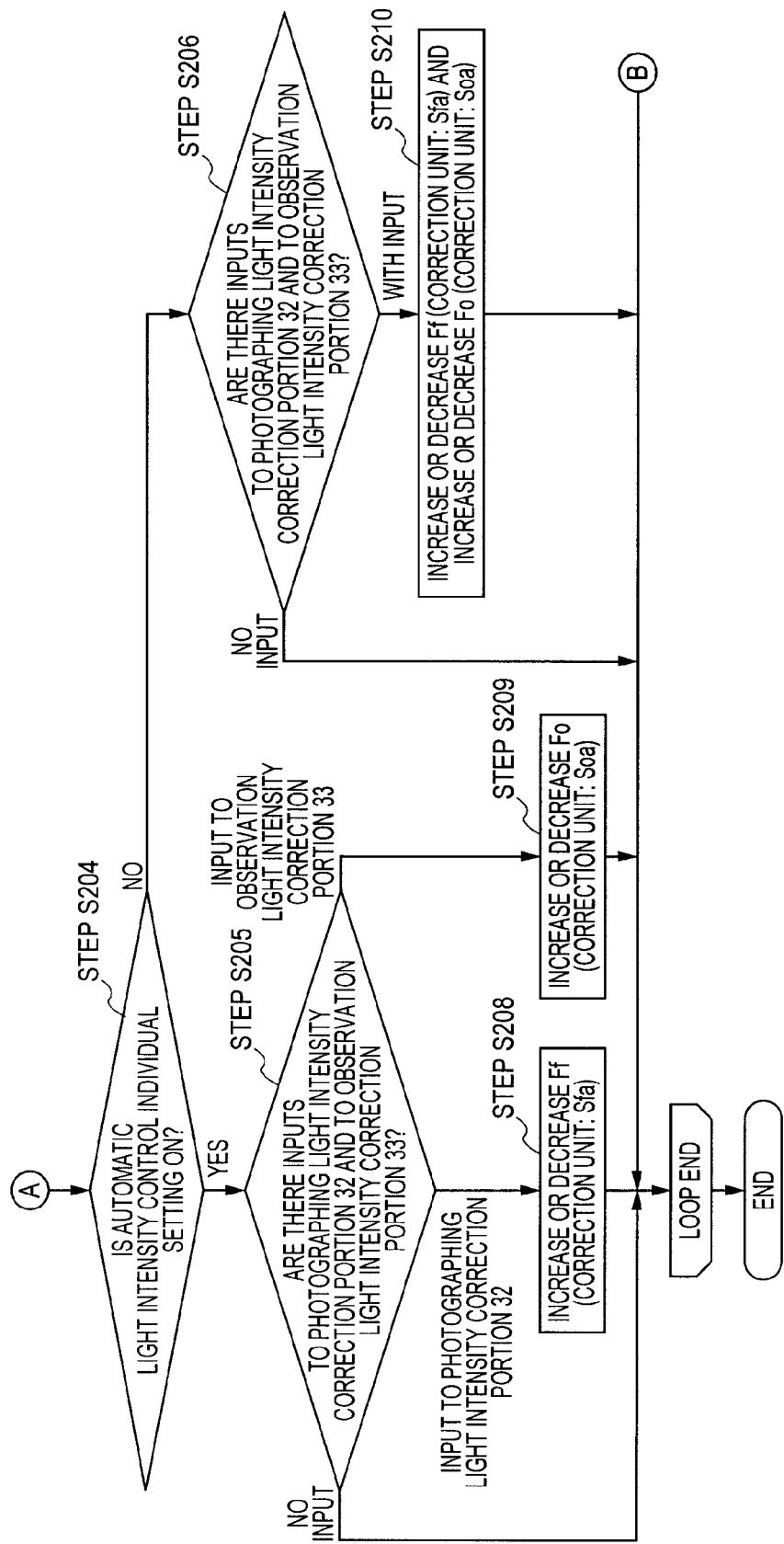
FIG. 4 is comprised of FIGS. 4A and 4B showing a flowchart illustrating a changing process of a photographing light intensity correction value and an observation light intensity correction value.

In order to describe Step S104 and the subsequent steps of FIG. 3, it is necessary to first describe how the photographing light intensity correction value Ff and the observation light intensity correction value Fo are changed. Therefore, FIGS. 4A and 4B are temporarily referred to for the description, and the changing process of the photographing light intensity correction value Ff and the observation light intensity correction value Fo is described. Here, for convenience of description, the changing process of the photographing light intensity correction value Ff and the observation light intensity correction value Fo illustrated in FIGS. 4A and 4B is described after Step S103 of FIG. 3 is described. Actually, however, the process illustrated in FIGS. 4A and 4B is performed in an asynchronous manner with the process of FIG. 3 in a period from Step S101 to before Step S109 illustrated in FIG. 3.

Hereinafter, the flowchart illustrated in FIGS. 4A and 4B is described. In Step S200, as described above, the changing process of the photographing light intensity correction value Ff and the observation light intensity correction value Fo is performed repeatedly in a period from Step S101 to before S109 illustrated in FIG. 3.

In Step S201, the central control unit 23 determines whether or not automatic light intensity control ON/OFF switching by input of the light intensity control switching portion 34 has been detected. When the automatic light intensity control ON/OFF switching has been detected, the central control unit 23 initializes the photographing light intensity correction value Ff and the observation light intensity correction value Fo in Step S202.

The process after that is branched according to conditions. First, there is described a process performed in the case where the observation light intensity and the photographing light intensity that are default setting in this embodiment are corrected individually and are automatically controlled. In this series of process, the photographing light intensity correction value Ff can be increased or decreased by the photographing light intensity correction portion 32, and the observation light intensity correction value Fo can be increased or decreased by the observation light intensity correction portion 33.

Figure 5:
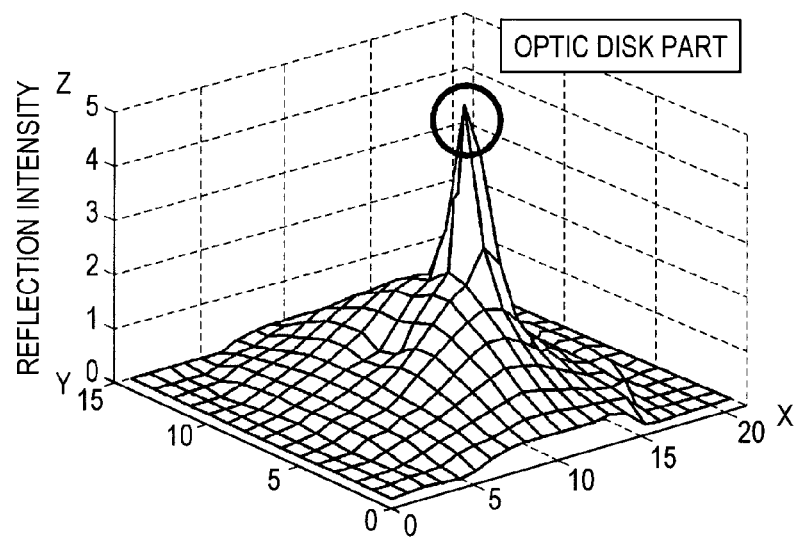
FIG. 5 is a diagram illustrating an example of reflection intensity of each fundus part when a fundus image is taken with a photographing light source.

Here, a purpose of increase and decrease of the photographing light intensity correction value Ff and the observation light intensity correction value Fo performed by the operator is described. First, a purpose of increasing or decreasing the photographing light intensity correction value Ff is described. FIG. 5 is a diagram illustrating an example of the reflection intensity in each fundus part when the fundus image is taken with the photographing light source 12. The fundus image is illustrated in XY plane, and the reflection intensity is illustrated in Z axis direction. As illustrated in FIG. 5, when the fundus is irradiated with the light source having a wavelength range that is usually used for the photographing light source 12, a fundus part called an optic disk part has outstandingly high reflection. Therefore, the optic disk part may be exposed excessively depending on the photographing light intensity. Therefore, if the operator wants to avoid the excessive exposure of the optic disk part, the photographing light intensity correction value Ff is set to a low value so as to prevent excessive light intensity. On the other hand, if the light intensity of the photographing light source 12 is increased, an image with a better SN ratio can be obtained. For instance, if the operator does not need information of the optic disk part so much, the photographing light intensity correction value Ff may be set to a high value for photographing. In addition, for other reason than the above-mentioned reason, for example, if fine adjustment of the light intensity is wanted due to a disease of the eye E to be inspected or the like, the photographing light intensity correction value Ff is adjusted so as to support the fine adjustment.

Next, a purpose of increasing or decreasing the observation light intensity correction value Fo is described. First, the operator performs roughly two things under the observation light. One is the fundus observation under the observation light. While the image taken under the photographing light is a still image, a moving image is used for an observed image. For this reason, the fundus observation may be performed under the observation light. The other thing is alignment. The operator refers to the alignment index that is emitted from the WD light source 15 and is projected to the cornea Ep, to thereby perform the alignment between the eye E to be inspected and the optical portion of the fundus camera.

Figure 6A:
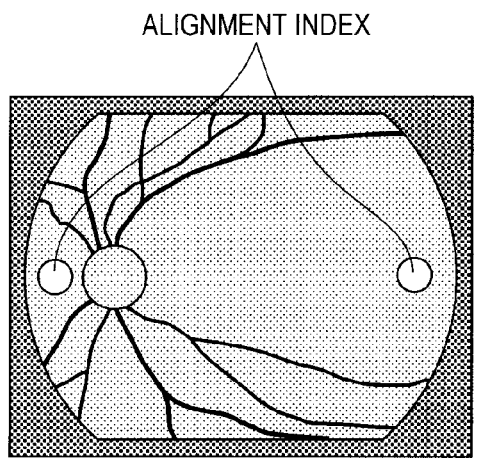
FIGS. 6A and 6B are diagrams illustrating fundus images taken with the observation light.
Figure 6B:
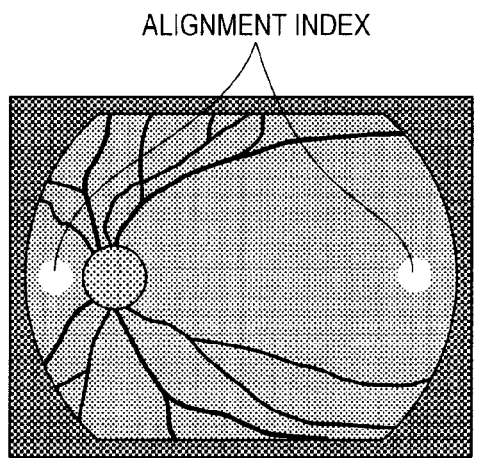

FIGS. 6A and 6B are diagrams illustrating fundus images under the observation light, in which the fundus image and the alignment index are illustrated. FIG. 6A illustrates the fundus image in the case where the observation light is bright, and FIG. 6B illustrates the fundus image in the case where the observation light is dark. For instance, if the operator wants to observe the fundus image under the observation light, the observation light intensity correction value Fo needs to be set to a high value so that a bright fundus image is obtained as illustrated in FIG. 6A. In addition, when alignment is performed, for example, the observation light intensity correction value Fo needs to be set to a low value to obtain the dark fundus image as illustrated in FIG. 6B so that the alignment index, which has a constant light intensity, can be seen clearly.

As described above, the reason for correcting the photographing light intensity and the reason for correcting the observation light intensity are different to each other. Therefore, in this embodiment, the photographing light intensity correction portion 32 and the observation light intensity correction portion 33 are provided separately, and hence the light intensity correction can be performed individually.

Hereinafter, a process of correcting the observation light intensity and the photographing light intensity individually is described with reference to the individual steps. In Step S203, the central control unit 23 determines whether the automatic light intensity control is ON or OFF. The ON/OFF of the automatic light intensity control is switched by the light intensity control switching portion 34. When the automatic light intensity control is ON, the process flow goes to Step S204. When the automatic light intensity control is OFF, the process flow goes to Step S207. First, the case where the automatic light intensity control is ON is described.

In Step S204, the central control unit 23 determines whether the light intensity correction performed by the operator of the automatic light intensity control is set so that the observation light intensity and the photographing light intensity can be changed individually or is set so that the observation light intensity and the photographing light intensity are changed in a synchronized manner. Whether the setting is for the individual change or for the change in a synchronized manner can be determined by the operator using a setting portion (not shown) before photographing. In the case of the setting for the individual change, the process flow goes to Step S205. In the case of the setting for the change in a synchronized manner, the process flow goes to Step S206. First, the case of the setting for the individual change, which is a default setting in this embodiment, is described.

In Step S205, the central control unit 23 detects inputs of the photographing light intensity correction portion 32 and the observation light intensity correction portion 33. When there is no input, the central control unit 23 does nothing. When an input from the photographing light intensity correction portion 32 is detected, the central control unit 23 increases or decreases the photographing light intensity correction value Ff according to the input from the photographing light intensity correction portion 32 in Step S208. On the other hand, when an input from the observation light intensity correction portion 33 is detected, the central control unit 23 increases or decreases the observation light intensity correction value Fo according to the input from the observation light intensity correction portion 33 in Step S209.

In other words, in Step S208, the central control unit 23 increases the photographing light intensity correction value Ff by Sfa, which is a unit of correction, when there is an input of increasing correction from the photographing light intensity correction portion 32, and decreases the photographing light intensity correction value Ff by the unit of correction Sfa when there is an input of decreasing correction. The photographing light intensity correction value Ff increases or decreases according to the input in the range from a lower limit $Ff_{min}$ of the photographing light intensity correction value to an upper limit $Ff_{max}$ of the photographing light intensity correction value. However, for example, the photographing light intensity correction value Ff is not increased or decreased even if there is an input of the increasing correction when Ff is the upper limit $Ff_{max}$. This process is omitted in FIGS. 4A and 4B for simple description.

In Step S209, similarly to the photographing light intensity correction value Ff, the central control unit 23 increases the observation light intensity correction value Fo by a unit of correction Soa according to an input of increasing correction from the observation light intensity correction portion 33, and decreases the observation light intensity correction value Fo by the unit of correction Soa according to an input of decreasing correction. The observation light intensity correction value Fo is also increased or decreased according to an input in the range from a lower limit $Fo_{min}$ of the observation light intensity correction value to an upper limit $Fo_{max}$ of the observation light intensity correction value. This process is also omitted in FIGS. 4A and 4B for simple description.

Next, the process branched in Step S204, which is performed in the case of the setting in which the observation light intensity and the photographing light intensity are changed in a synchronized manner, is described. In this series of process, for example, if one of the photographing light intensity correction portion 32 and the observation light intensity correction portion 33 is operated, both the photographing light intensity correction value Ff and the observation light intensity correction value Fo are changed in a synchronized manner.

In this process, the operator can increase or decrease the photographing light intensity correction value Ff and the observation light intensity correction value Fo in a synchronized manner. Therefore, compared with the setting for the individual change, flexibility of the light intensity correction is restricted, but the light intensity correction can be performed by a simple operation intuitively by the operator because the taken image becomes brighter when the observed image is made brighter, for example.

In the setting in which the observation light intensity and the photographing light intensity are changed in a synchronized manner, the process flow goes from Step S204 to Step S206. In Step S206, the central control unit detects inputs of the photographing light intensity correction portion 32 and the observation light intensity correction portion 33. When there is no input, the central control unit 23 does nothing. On the other hand, when the central control unit 23 detects one of inputs of the photographing light intensity correction portion 32 and the observation light intensity correction portion 33, the process flow goes to Step S210, in which both the photographing light intensity correction value Ff and the observation light intensity correction value Fo are increased or decreased in a synchronized manner.

Specifically, in Step S210, when there is an input of increasing correction in one of the photographing light intensity correction portion 32 and the observation light intensity correction portion 33, the central control unit 23 increases the photographing light intensity correction value Ff by the unit of correction Sfa and increases the observation light intensity correction value Fo by the unit of correction Soa. On the other hand, when there is an input of decreasing correction in one of the photographing light intensity correction portion 32 and the observation light intensity correction portion 33, the central control unit 23 decreases the photographing light intensity correction value Ff by the unit of correction Sfa and decreases the observation light intensity correction value Fo by the unit of correction Soa. Setting ranges of values of the units of correction Sfa and Soa, the photographing light intensity correction value Ff, and the observation light intensity correction value Fo are the same as in the case of the setting for the individual change in Step S208 and Step S209.

Next, the process branched in Step S203, which is performed in the case where the manual light intensity control is performed, is described. In this series of process, the photographing light intensity correction value Ff can be increased or decreased by the photographing light intensity correction portion 32, and the observation light intensity correction value Fo can be increased or decreased by the observation light intensity correction portion 33. In addition, the controlled photographing light intensity Pf becomes Ff, and the controlled observation light intensity Po becomes Fo because the automatic light intensity control is not performed.

When the automatic light intensity control is OFF, and the manual light intensity control is performed, the process flow goes from Step S203 to Step S207. In Step S207, the central control unit 23 detects inputs of the photographing light intensity correction portion 32 and the observation light intensity correction portion 33. When there is no input, the central control unit 23 does nothing. When there is an input from the photographing light intensity correction portion 32, the central control unit 23 increases or decreases the photographing light intensity correction value Ff in Step S211. In addition, when there is an input from the observation light intensity correction portion 33, the central control unit 23 increases or decreases the observation light intensity correction value Fo in Step S212.

Note that a difference between the manual light intensity control and the automatic light intensity control is the setting range of the photographing light intensity correction value Ff. In the manual light intensity control, the setting range of the photographing light intensity correction value Ff is the same as the setting range of the controlled photographing light intensity value Pf. In addition, when the setting range is changed, the unit of correction also becomes different from that in the automatic light intensity control. The central control unit 23 increases or decreases the photographing light intensity by a unit of correction Sfm according to an input from the photographing light intensity correction portion 32.

In Step S212, the central control unit 23 increases or decreases the observation light intensity correction value Fo according to an input from the observation light intensity correction portion 33. The setting range of the observation light intensity correction value Fo becomes the same as the setting range of the controlled observation light intensity value Po, and a unit of correction for the observation light intensity becomes Som, while others are the same as in Step S209.

The flowchart illustrated in FIG. 3 is referred to again. In Step S104, the central control unit 23 determines whether the automatic light intensity control is ON or OFF. As described above, the ON/OFF of the automatic light intensity control is switched by the light intensity control switching portion 34. When the automatic light intensity control is ON, the process flow goes to Step S105. When the automatic light intensity control is OFF, the process flow goes to Step S106.

In Step S105, the photographing light intensity calculation operation portion 26 determines a fundus reflectance R of the eye E to be inspected from the photometry value S of the observation light obtained by the photometry value calculation portion 19 and the light intensity value of the observation light from the observation light source 14 controlled by the observation light source control portion 25. The fundus reflectance R means a ratio of the light intensity of the reflected light from the fundus to the light intensity of the observation light irradiating the eye E to be inspected. The photographing light intensity calculation operation portion 26 stores a table in which the fundus reflectance R and the photographing light intensity for the fundus to be imaged with an appropriate exposure are associated to each other. The photographing light intensity calculation operation portion 26 refers to the above-mentioned table with respect to the fundus reflectance R so as to obtain the standard photographing light intensity Pfs for the fundus to be imaged with the appropriate exposure.

In addition, in Step S105, the photographing light intensity calculation operation portion 26 adds the photographing light intensity correction value Ff increased or decreased in Steps S201 to S208 or in Steps S201 to S210 and a value of the standard photographing light intensity Pfs so as to calculate the controlled photographing light intensity Pf. Note that in Step S105, the observation light intensity calculation operation portion 27 adds the observation light intensity correction value Fo increased or decreased in Steps S201 to S209 or in Steps S201 to S210 and a value of the standard observation light intensity Pos so as to calculate the controlled observation light intensity Po. Note that the observation light intensity calculation operation portion 27 stores a table in which the fundus reflectance R and the observation light intensity for the fundus to be observed with an appropriate exposure are associated to each other. The observation light intensity calculation operation portion 27 refers to the above-mentioned table with respect to the fundus reflectance R so as to obtain the standard observation light intensity Pos for the fundus to be observed with an appropriate exposure.

In Step S106, the photographing light intensity calculation operation portion 26 substitutes the photographing light intensity correction value Ff increased or decreased in Steps S201 to S211 into the controlled photographing light intensity Pf. In addition, in Step S106, the observation light intensity calculation operation portion 27 substitutes the observation light intensity correction value Fo increased or decreased in Steps S201 to S212 into the controlled observation light intensity Po.

The process flow goes to Step S107 via Step S105 or Step S106. In Step S107, the central control unit 22 stores the controlled photographing light intensity Pf calculated by the photographing light intensity calculation operation portion 26 in the light intensity memory 29. In addition, in Step S107, the observation light source control portion 25 controls the observation light source 14 to have the controlled observation light intensity Po calculated by the observation light intensity calculation operation portion 27. The observation light source 14 irradiates the eye E to be inspected with the observation light having the controlled light intensity.

When the alignment and the focus adjustment are finished, the inspector presses the photographing switch 31. The central control unit 22 determines whether or not the photographing switch 31 is pressed (Step S108). When the photographing switch 31 is not pressed, the process flow goes back to Step S102. On the other hand, when the photographing switch 31 is pressed, the process flow goes to Step S109.

In Step S109, the photographing light source control portion 24 controls the photographing light source 12 to emit the photographing light at the controlled photographing light intensity Pf stored in the light intensity memory 29. The photographing light source 12 irradiates the eye E to be inspected by the photographing light having the controlled light intensity. The light beam emitted from the photographing light source 12 irradiates the fundus Er of the eye E to be inspected.

In Step S110, the photographing portion 22 receives the photographing light so as to take the fundus image. The light beam emitted from the photographing light source 12 irradiates the fundus Er, and the reflected and scattered light beam from the fundus Er goes out from the eye E to be inspected through the pupil Ep and reaches the photographing element 5. The photographing element 5 receives the photographing light so as to generate an electronic signal. The A/D converter element 17 converts the generated electronic signal into a digital signal, and the central control unit 23 stores the digital signal as still image data in the image memory 28.

As described above, in this embodiment, the fundus reflectance R of the eye E to be inspected is determined by measuring the reflected light from the fundus, and the photographing light intensity and the observation light intensity are calculated for photographing and observation with appropriate exposure. In addition to this, in this embodiment, the operator can adjust the observation light source and the photographing light source individually according to the purpose, the use, or the like. In other words, in this embodiment, the standard photographing light intensity Pfs and the standard observation light intensity Pos calculated from the fundus reflectance R can be corrected automatically by the correction value input by the operator. Therefore, if the operator inputs the correction value according to the purpose, the use, or the like of the photographing or the observation, the observation light and the photographing light are automatically controlled to have appropriate light intensities according to the purpose or the like, and hence appropriate fundus inspection can be performed.

Next, other embodiments of the present invention are described. In the above-mentioned embodiment, the photographing light source 12 is a wide-band wavelength light source of 420 to 750 nm, and the observation light source 14 is substantially a single wavelength of 850 nm or a light source having a very narrow wavelength band, but another light source having another wavelength band may be adopted. In addition, if the wavelength band of the photographing light source 12 overlaps largely with the wavelength band of the observation light source 14, a structure in which both the light sources are disposed on the same optical axis may be adopted.

In addition, in the above-mentioned embodiment, the shutter is opened in a period from before light emission until after light emission of the observation light source 14 and the photographing light source 12, and the observation light source 14 adjusts its light intensity so that the light intensity of the photographing light to be received by the photographing element 5 is adjusted. In addition, in the above-mentioned embodiment, the shutter is opened in a period from before light emission until after light emission of the observation light source 14 and the photographing light source 12, and the photographing light source 12 adjusts the period of time for emitting the photographing light so that the light intensity of the photographing light to be received by the photographing element 5 is adjusted. However, the present invention is not limited to this structure, and the light intensity to be received by the sensor may be adjusted by inserting or removing a mask or a filter in the optical path according to a desired exposure. In addition, the light intensity of the photographing light source 12 reaching the sensor may be adjusted by adjusting the light intensity or a period of time for opening the shutter (shutter speed).

In addition, in the above-mentioned embodiment, the photographing light intensity correction portion 32 is constituted of two independent switches to support inputs of increasing correction and decreasing correction, but a slide switch or a seesaw switch may be adopted so that a single switch can be used for both the increasing correction and the decreasing correction. Note that the same is true for the observation light intensity correction portion 33.

In addition, the functions of the operation portion 30 in the above-mentioned embodiment may be changed by control of the central control unit 23 or by individual dials or buttons disposed for individual functions. In addition, the positional alignment of the main body portion of the fundus camera performed by the joystick or the dial may be performed automatically by the central control unit 23. Further, a configuration in which initial values of the photographing light intensity correction value Ff and the observation light intensity correction value Fo can be set by the operator using a setting unit may be adopted.

In the above-mentioned embodiment, the switching between the setting in which the observation light intensity and the photographing light intensity can be changed individually and the setting in which the observation light intensity and the photographing light intensity are changed in a synchronized manner is performed by the setting portion (not shown), but a member for this setting may be provided as a switch or the like in the operation portion 30.

In the above-mentioned embodiment, the central control unit 23, the image memory 28, the photographing light intensity calculation operation portion 26, the observation light intensity calculation operation portion 27, the operation portion 30, the photographing light intensity correction portion 32, the observation light intensity correction portion 33, and the light intensity control switching portion 34 are included in the fundus camera 100. However, a part or a whole of the above-mentioned structure may be carried by an external computer connected to the fundus camera 100.

Further, the present invention is also implemented by executing the following processing. Specifically, in this processing, software (program) for implementing the functions of the above-mentioned embodiment is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-194512, filed Aug. 31, 2010, which is hereby incorporated by reference herein in its entirety.

What is claimed is:

1. A light intensity control apparatus, comprising:
an acquisition unit for acquiring a correction value of a light intensity of a first light source for observing a fundus and a correction value of a light intensity of a second light source for photographing the fundus, the correction values being changed in accordance with an instruction input by an inspector;
a first control unit for controlling the light intensity of the first light source based on photometry information obtained by a photometry unit, the light intensity of the first light source obtained in the measurement by the photometry unit, and the changed correction value of the light intensity of the first light source, wherein the photometry unit measures reflected light from the fundus under illumination by the first light source; and
a second control unit for controlling the light intensity of the second light source based on the photometry information obtained by the photometry unit, the light intensity of the first light source obtained in the measurement by the photometry unit, and the changed correction value of the light intensity of the second light source.

2. A light intensity control apparatus according to claim 1, wherein the first control unit is configured to:
obtain the light intensity of the first light source, which corresponds to a reflection characteristic of the fundus, the reflection characteristic being a ratio of a light intensity of the reflected light from the fundus under illumination of the first light source, which is indicated by the photometry information, with respect to the light intensity of the first light source obtained in the measurement by the photometry unit; and
control the light intensity of the first light source based on the obtained light intensity of the first light source and the changed correction value of the light intensity of the first light source.

3. A light intensity control apparatus according to claim 1, wherein the second control unit is configured to:
obtain the light intensity of the second light source, which corresponds to a reflection characteristic of the fundus, the reflection characteristic being a ratio of a light intensity of the reflected light from the fundus under illumination of the first light source, which is indicated by the photometry information, with respect to the light intensity of the first light source obtained in the measurement by the photometry unit; and
control the light intensity of the second light source based on the obtained light intensity of the second light source and the changed correction value of the light intensity of the second light source.

4. A light intensity control apparatus according to claim 1, further comprising a switching unit for switching ON and OFF of automatic light intensity control,
wherein, when the switching unit switches the automatic light intensity control to be ON, the first control unit and the second control unit are activated.

5. A light intensity control apparatus according to claim 1, further comprising:
a first input unit for receiving an input concerning the correction value of the light intensity of the first light source;
a second input unit for receiving an input concerning the correction value of the light intensity of the second light source; and
a changing unit for changing both the correction value of the light intensity of the first light source and the correction value of the light intensity of the second light source in a synchronized manner, according to an input received by one of the first input unit and the second input unit.

6. A light intensity control apparatus according to claim 1, further comprising a photographing unit for outputting image data for observing the fundus based on the reflected light from the fundus under illumination of the first light source, and outputting image data for photographing the fundus based on reflected light from the fundus under illumination of the second light source,
wherein the photometry unit measures the reflected light from the fundus under illumination of the first light source based on the image data output from the photographing unit under illumination of the first light source.

7. A light intensity control method for a light intensity control apparatus, the method comprising:
an acquiring step of acquiring a correction value of a light intensity of a first light source for observing a fundus and a correction value of a light intensity of a second light source for photographing the fundus, the correction values being changed in accordance with an instruction input by an inspector;
a light measuring step of measuring reflected light from the fundus under illumination of the first light source;
a first control step of controlling the light intensity of the first light source based on photometry information obtained in the light measuring step, the light intensity of the first light source obtained in the measurement of the light measuring step, and the changed correction value of the light intensity of the first light source; and
a second control step of controlling a light intensity of the second light source, based on the photometry information obtained in the light measuring step, the light intensity of the first light source obtained in the measurement of the light measuring step, and the changed correction value of the light intensity of the second light source.

8. A recording medium having recorded thereon a program for causing a computer to perform the steps of the light intensity control method according to claim 7.

9. An ophthalmologic apparatus, comprising:
an observation light source for observing an eye to be inspected;
a photographing light source for photographing the eye to be inspected;
an acquisition unit for acquiring a correction value of a light intensity of the photographing light source, the correction value being changed in accordance with an instruction input by an inspector;

a photometry unit for measuring return light from the eye to be inspected, which is irradiated by observation light from the observation light source; and a control unit for controlling a light intensity of the photographing light source based on photometry information obtained by the photometry unit and the changed correction value of the light intensity of the photographing light source.

10. An ophthalmologic apparatus according to claim 9, wherein the control unit includes:

a first control unit for controlling the light intensity of the observation light source based on the photometry information obtained by the photometry unit and an observation light intensity correction value; and a second control unit for controlling the light intensity of the photographing light source based on the photometry information obtained by the photometry unit and a photographing light intensity correction value.

11. An ophthalmologic apparatus according to claim 10, further comprising a setting unit for setting the photographing light intensity correction value based on brightness of an optic disk of the fundus of the eye to be inspected.

12. An ophthalmologic apparatus according to claim 10, further comprising a setting unit for setting the observation light intensity correction value based on brightness of a fundus image of the fundus of the eye to be inspected, which is based on the observation light, and brightness of an alignment index.

13. An ophthalmologic apparatus, comprising:

an observation light source for observing an eye to be inspected;

an acquisition unit for acquiring a correction value of a light intensity of the observation light source, the correction value being changed in accordance with an instruction input by an inspector;

a photometry unit for measuring return light from the eye to be inspected, which is irradiated by observation light from the observation light source; and a control unit for controlling a light intensity of the observation light source based on photometry information obtained by the photometry unit and the changed correction value.

14. An ophthalmologic method, comprising the steps of:

acquiring a correction value of a light intensity of a photographing light source, the correction value being changed in accordance with an instruction input by an inspector;

measuring, by a photometry unit, return light from an eye to be inspected, which is irradiated by observation light from an observation light source; and controlling a light intensity of the photographing light source based on photometry information obtained by the photometry unit and the changed correction value of the light intensity of the photographing light source.

15. A recording medium having recorded thereon a program for causing a computer to perform the steps of the ophthalmologic method according to claim 14.

16. An ophthalmologic method, comprising the steps of:

acquiring a correction value of a light intensity of an observation light source, the correction value being changed in accordance with an instruction input by an inspector;

measuring, by a photometry unit, return light from an eye to be inspected, which is irradiated by observation light from the observation light source; and controlling a light intensity of the observation light source based on photometry information obtained by the photometry unit and the changed correction value.

17. A recording medium having recorded thereon a program for causing a computer to perform the steps of the ophthalmologic method according to claim 16.

* * * * *